United States Patent [19]

Takago et al.

[11] Patent Number: 4,587,354

[45] Date of Patent: May 6, 1986

[54] NOVEL ORGANOSILICON COMPOUND AND A ROOM TEMPERATURE CURABLE ORGANOPOLYSILOXANE COMPOSITION CONTAINING THE SAME

[75] Inventors: Toshio Takago; Yoshio Inoue; Masami Terashima; Shiniti Sato, all of Gunma, Japan

[73] Assignee: Shin-Etsu Chemical, Co., Ltd., Tokyo, Japan

[21] Appl. No.: 591,380

[22] Filed: Mar. 20, 1984

[30] Foreign Application Priority Data

Mar. 28, 1983 [JP] Japan ................................ 58-51810
Apr. 4, 1983 [JP] Japan ................................ 58-59031

[51] Int. Cl.$^4$ .......................... C07F 7/08; C07F 7/10
[52] U.S. Cl. ................................. 556/417; 556/452; 556/460; 556/461; 556/456
[58] Field of Search ............... 556/417, 452, 460, 461, 556/456

[56] References Cited

U.S. PATENT DOCUMENTS

| | | | |
|---|---|---|---|
| 3,360,538 | 12/1967 | Ashby | 556/460 X |
| 3,373,138 | 3/1968 | Brown | 556/460 X |
| 3,555,065 | 1/1971 | Hampton | 556/460 |
| 3,575,921 | 4/1971 | Lee | 556/460 X |
| 4,308,393 | 12/1981 | Apotheker | 556/460 X |
| 4,539,418 | 9/1985 | Takago et al. | 556/460 X |

Primary Examiner—Paul F. Shaver
Attorney, Agent, or Firm—Toren, McGeady, Stanger, Goldberg & Kiel

[57] ABSTRACT

The invention discloses a novel cyclic organopolysiloxane compound having one or more of 3,3,3-trifluoropropyl groups and one or more of alkenyloxy groups, e.g. isopropenyloxy group of the formula —O—C(CH$_3$)=CH$_2$, each directly bonded to the silicon atom in a molecule. This novel organopolysiloxane compound is useful as a crosslinking agent for a hydroxy-terminated diorganopolysiloxane and a formulation of a room temperature curable organopolysiloxane composition capable of giving a rubbery elastomer by curing is proposed comprising, each in a limited proportion, (a) a hydroxy-terminated diorganopolysiloxane, (b) the above disclosed novel cyclic organopolysiloxane having 2 or 3 alkenyloxy groups, (c) a second cyclic organopolysiloxane having 2 or 3 alkenyloxy groups each directly bonded to the silicon atom in a molecule and (d) a guanidino-containing organosilicon compound, e.g. 3-(tetramethylguanidino)propyl trimethyl silane, as a curing accelerator. This room temperature curable composition exhibits excellent curability and free from the problem of the formation of noxious condensation products as in the conventional RTV silicone rubber compositions.

2 Claims, 4 Drawing Figures

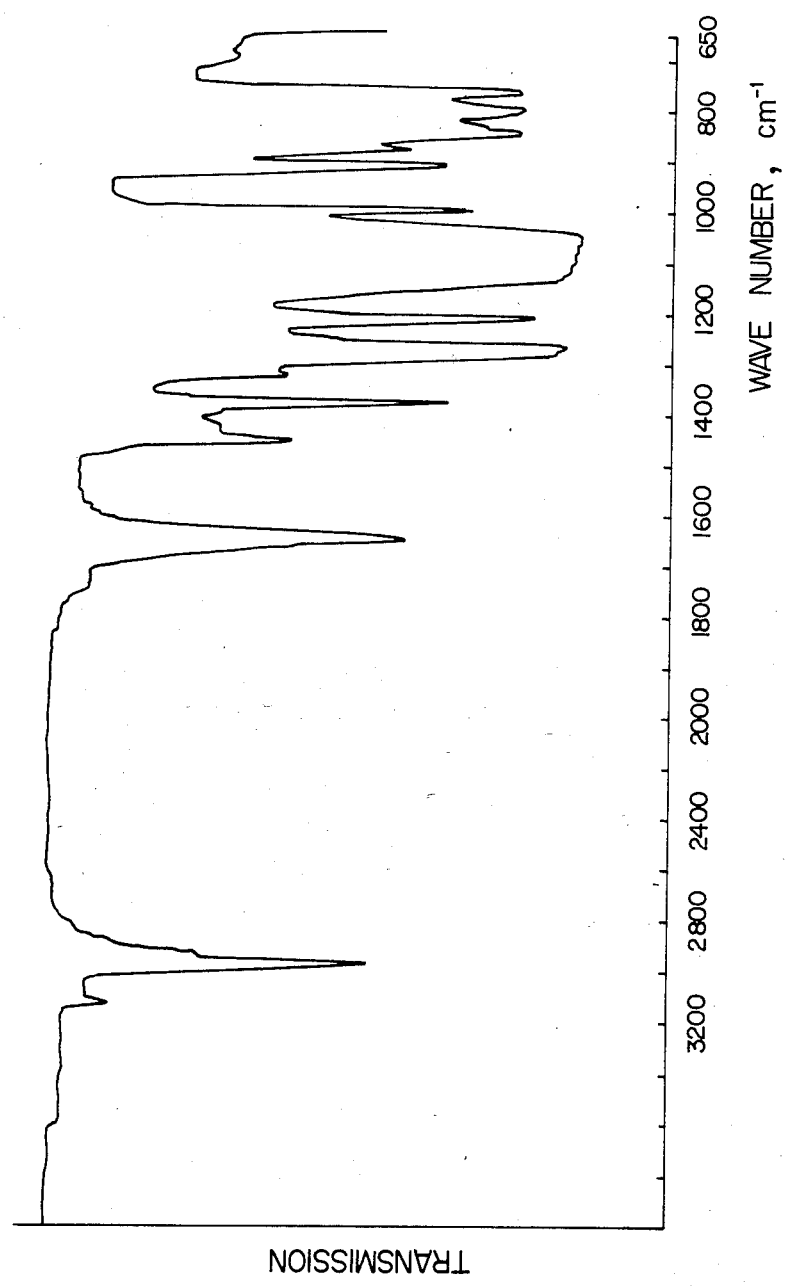

NOVEL ORGANOSILICON COMPOUND AND A ROOM TEMPERATURE CURABLE ORGANOPOLYSILOXANE COMPOSITION CONTAINING THE SAME

BACKGROUND OF THE INVENTION

The present invention relates to a novel organosilicon compound and a room temperature curable organopolysiloxane composition with improved curability containing the novel organosilicon compound as an essential component.

There are known several types of room temperature curable organopolysiloxane compositions or so-called RTV silicone rubbers, i.e. room temperature vulcanizable silicone rubber compositions, curable at room temperature into a rubbery elastomer. These RTV silicone rubber compositions are classified from the standpoint of practical use into two classes of the so-called two-package type and one-package type ones. The compositions of the former type are supplied in two packages containing different components or premixes of components to be blended directly before use in order to avoid premature curing while the compositions of the latter type are supplied as a read-mixed blend of all of the components by virtue of the storage stability thereof and usable without blending of the components before use.

In connection with the mechanisms involved in the crosslinking reaction, RTV silicone rubber compositions are further classified into several classes. For exammple, many of the RTV silicone rubber compositions are cured by the mechanism of a condensation reaction producing different condensation products such as carboxylic acids, e.g. acetic acid, alcohol compounds, aminoxy compounds, amine compounds, oxime compounds and the like according to the types of the functional groups pertaining to the condensation reaction. The carboxylic acid, aminoxy, amine and oxime compounds are, however, toxic or corrosive so that the RTV silicone rubber compositions emitting these noxious gases by curing cannot be used in contact with metals and must be used under good ventilation. The RTV silicone rubber compositions of the dealcoholation type are of course free from the problem of the emission of noxious gases but, on the other hand, disadvantageous due to the insufficient storage stability and the relatively low curing velocity as well as poor mechanical properties of the cured rubber with fragility.

Further, it is a usual practice that some of the RTV silicone rubber compositions are admixed with certain curing accelerators or curing cocatalysts such as titanium alkoxide compounds, metal salts of organic acids and the like. The addition of such an auxiliary ingredient, however, involves serious disadvantages caused by the adverse effects of the ingredient remaining in the cured rubber on the coloration and physical and chemical properties of the rubber even by setting aside the toxicity of some of the metallic components. In this regard, RTV silicone rubber compositions curable by the mechanism of deketonation condensation have been developed (see, for example, Japanese Patent Publications Nos. 51-39274, 51-39673 and 54-44669). Although these compositions are satisfactory in respects of the adhesiveness to the substrate surface and corrosiveness, they are not suitable for use where a large ultimate elongation of the cured rubber is desired.

SUMMARY OF THE INVENTION

It is therefore an object of the present invention to provide a novel and improved room temperature curable organopolysiloxane composition free from the above described problems and disadvantages in the prior art RTV silicone rubber compositions by introducing, as an essential component, a functional organosilicon compound hitherto not known or not used as a component of a RTV silicone rubber composition.

Another object of the present invention is to provide a novel organosilicon compound not described in any prior art literatures and useful as an essential component in the inventive room temperature curable organopolysiloxane compositions.

Thus, the novel organosilicon compound provided by the invention is a cyclic organopolysiloxane compound represented by the general formula

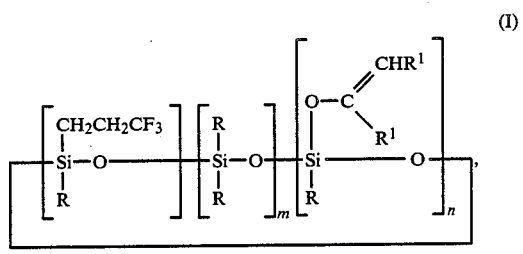

in which the groups denoted by R are each a halogen- or cyano-substituted or unsubstituted monovalent hydrocarbon group having from 1 to 8 carbon atoms or a trimethylsiloxy group independently from the others, the groups denoted by $R^1$ are each a hydrogen atom or a substituted or unsubstituted monovalent hydrocarbon group having from 1 to 8 carbon atoms independently from the other, the suffix m is a number of 0, 1 or 2 and the suffix n is a number of 1, 2 or 3 with the proviso that m+n is 3 or 4.

The room temperature curable organopolysiloxane composition provided by the invention comprises:

(a) 100 parts by weight of a diorganopolysiloxane terminated at both molecular chain ends each with a hydroxy group directly bonded to the terminal silicon atom;

(b) from 0.01 to 25 parts by weight of a first cyclic organopolysiloxane represented by the above given general formula (I) in which the suffix n has a value of 2 or 3;

(c) from 0.01 to 25 parts by weight of a second cyclic organopolysiloxane represented by the general formula

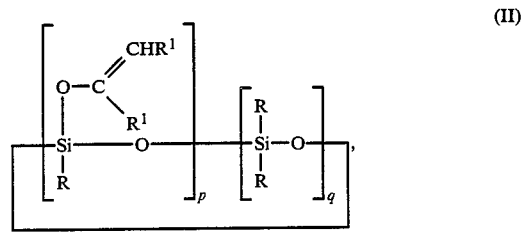

in which R and $R^1$ each have the same meaning as defined above, the suffix p is a number of 3, 4, 5 or 6 and the suffix q is zero or a positive integer with the proviso that p+q is 3, 4, 5 or 6; and (d) from 0.001 to 5 parts by weight of an organosilane or organopolysiloxane compound having, in a molecule, at least one guanidino group represented by the general formula (R²₂N—)₂C=N—, (III)

in which the groups denoted by R² are each a hydrogen atom or a monovalent hydrocarbon group.

BRIEF DESCRIPTION OF THE DRAWING

FIGS. 1, 2, 3 and 4 are each an infrared absorption spectrum of one of the novel cyclic organopolysiloxane compounds of the invention prepared in Examples 1, 2, 3 and 4, respectively.

DETAILED DESCRIPTION OF THE PREFERRED EMBODIMENTS

Figure 1:
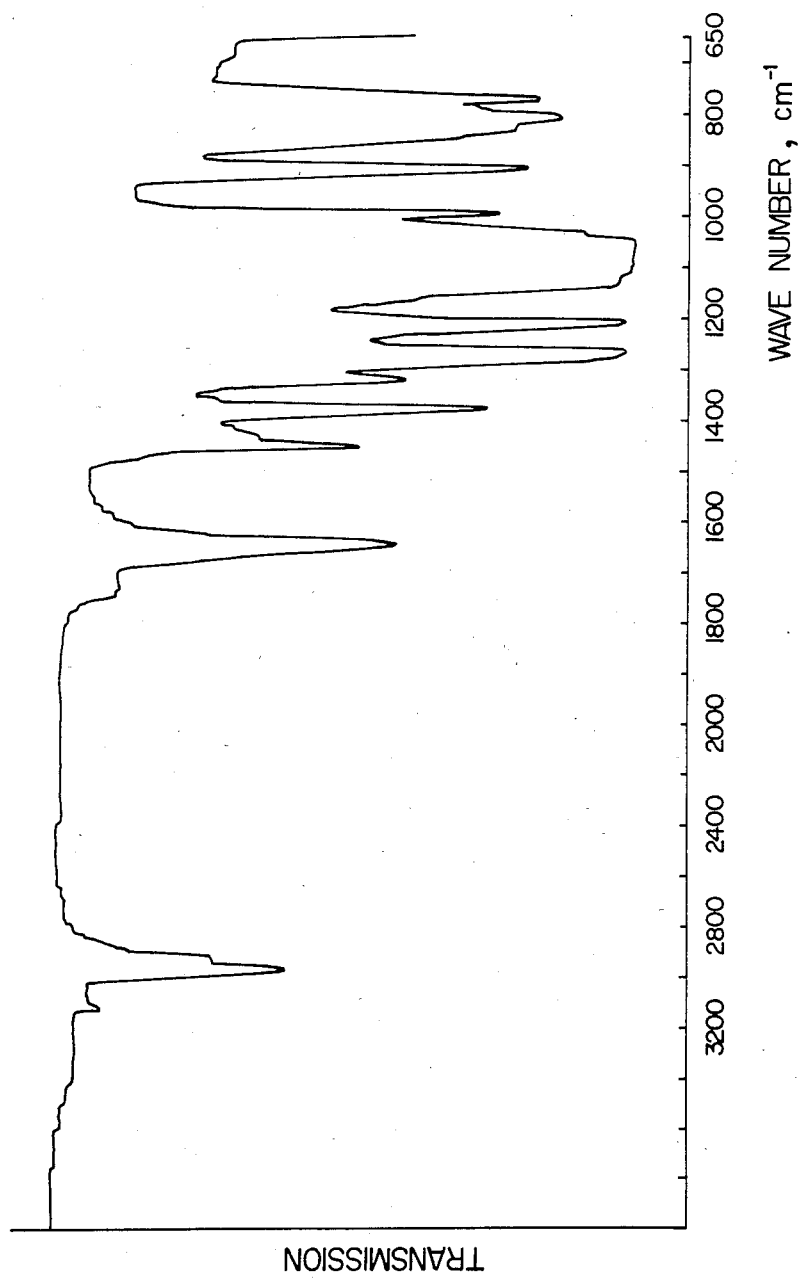

In the first place, description is given of the novel cyclic organopolysiloxane compound of the invention represented by the above given general formula (I). As is understood from this formula, the characteristic groups in this compound are the 3,3,3-trifluoropropyl group —CH₂CH₂CF₃ and alkenyloxy group —O—CR¹=CHR¹. When the groups denoted by the symbols R and R¹ are each an unsubstituted monovalent hydrocarbon group having from 1 to 8 carbon atoms, they can be each an alkyl group such as methyl, ethyl, propyl and butyl groups, cycloalkyl group such as cyclopentyl and cyclohexyl groups, alkenyl group such as vinyl, allyl and hexenyl groups, aryl group such as phenyl, tolyl and xylyl groups or aralkyl group such as benzyl and 2-phenylethyl groups. When they are each a halogen- or cyano-substituted hydrocarbon group, they can be each a chloromethyl, 3-chloropropyl, 3,3,3-trichloropropyl, 3,3,3-trifluoropropyl, chlorocyclohexyl, bromophenyl or the like halogen-substituted hydrocarbon group or 2-cyanoethyl, 3-cyanopropyl, 4-cyanobutyl, 2-cyanobutyl or the like cyano-substituted hydrocarbon group.

Exemplary of the inventive cyclic organopolysiloxane compounds are the compounds expressed by the following structural formulas although they are merely for exemplification and not for limitation in any way. In the following formulas, the symbols Me, Pr and pH denote methyl, propyl and phenyl groups, respectively.

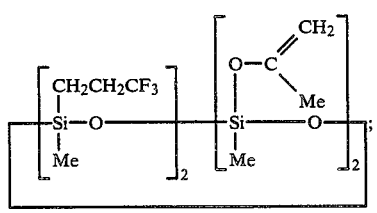

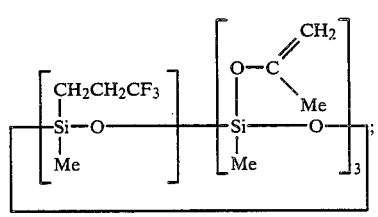

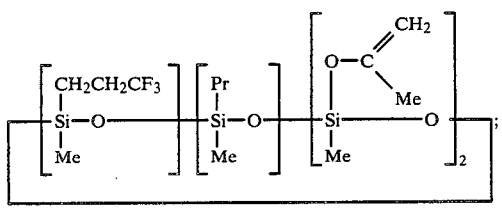

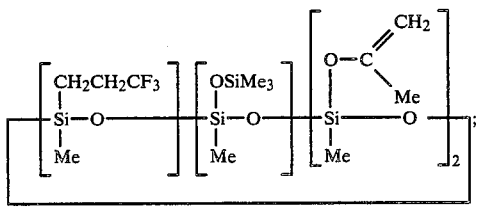

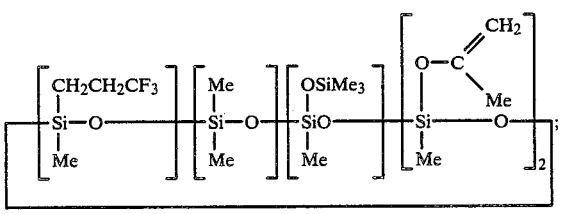

The above described cyclic organopolysiloxane compound of the invention can be synthesized starting, for example, with 1,3,5,7-tetramethyl cyclotetrasiloxane, which is referred to as H₄ hereinbelow, in three steps described below. It may be within presumption of those skilled in the art of silicones that the starting compound should be 1,3,5,7,9-pentamethyl cyclopentasiloxane when the final product is a cyclopentasiloxane in which m+n is equal to 4.

The first step is the partial chlorination to replace 2 or 3 of the silicon-bonded hydrogen atoms in H₄ to form tetramethyl dichlorocyclotetrasiloxane of the formula

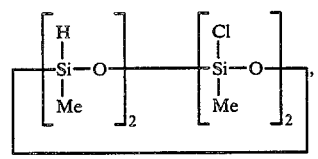

which is referred to as H₄Cl₂ hereinbelow, or tetramethyl trichlorocyclotetrasiloxane of the formula

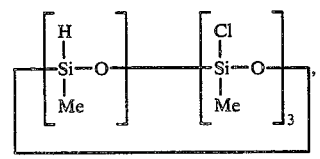

which is referred to as H₄Cl₃ hereinbelow.

The second step is the addition reaction of one or two kinds of ethylenically unsaturated hydrocarbon compounds including 3,3,3-trifluoropropene CH₂=CH—CF₃ with the silicon-bonded hydrogen atom or atoms in the above prepared H₄Cl₂ or H₄Cl₃ in the presence of a suitable catalyst to give a trifluoropropyl-substituted cyclotetrasiloxane of the formula

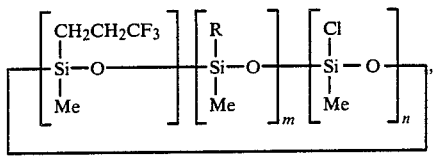

in which R has the same meaning as defined before, the suffix m is 0 or 1 and the sum of m+n is equal to 3. This addition reaction readily takes place at a temperature of 50° to 150° C. in the presence of a catalyst containing a metallic element belonging to the VIIIth group of the Periodic Table such as chloroplatinic acid, alcohol-modified chloroplatinic acid, complex compounds of chloroplatinic acid and an olefin, platinum black and solid platinum catalyst supported on a silica, alumina and the like carrier as well as complexes of rhodium and an olefin. These catalysts are used as dissolved in a suitable solvent such as alcohols, ketones, ethers and hydrocarbons, if possible.

The third step is the replacement reaction of the silicon-bonded chlorine atoms in the trifluoropropyl-substituted cyclotetrasiloxane prepared in the second step with alkenyloxy groups of the formula $-O-CR^1=CHR^1$, e.g. $-O-CMe=CH_2$. The reaction is undertaken in a reaction mixture composed of, for example, 1 mole of the fluoropropyl-containing cyclotetrasiloxane prepared in the second step, 27 moles of a ketone, e.g. acetone, N,N-dimethylformamide in an amount of 20% by weight of the acetone, triethylamine as an acid acceptor in an amount of 1.3 moles per mole of the silicon-bonded chlorine atoms in the reactant siloxane and 2 g of copper (I) chloride as a catalyst and the reaction mixture is heated at about 60° C. or higher under reflux of acetone for 4 to 10 hours. The reaction product obtained in this manner is expressed by the following formula

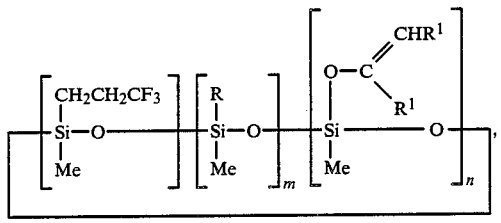

in which the suffixes m and n each have the same meaning as defined above and the alkenyloxy group $-O-CR^1=CHR^1$ is an isopropenyloxy group $-O-CMe=CH_2$ when the ketone is acetone.

When one of the groups denoted by R should be a trimethylsiloxy group of the formula $-O-SiMe_3$, the starting reactant H$_4$ should be replaced with 1-trimethylsiloxy-1,2,5,7-tetramethyl cyclotetrasiloxane, which is referred to as HT$_{41}$ hereinbelow, of the formula

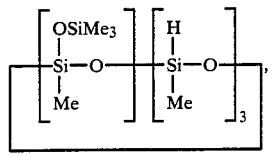

from which the first and the second step reactions described above give a cyclotetrasiloxane of the formula

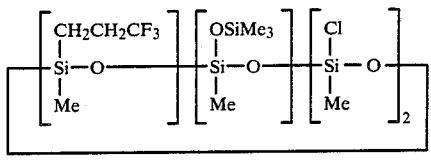

The dehydrochlorination reaction of this compound with a ketone, e.g. acetone, gives the desired trifluoropropyl- and alkenyloxy-substituted cyclotetrasiloxane.

The above described trifluoropropyl- and alkenyloxy-substituted cyclopolysiloxane is possibly useful as a crosslinking agent of a diorganopolysiloxane having silicon-bonded hydroxy groups at the terminals when the suffix n in the general formula of the compound is 2 or 3. Noting this possibility, in particular, the inventors have continued extensive investigations to establish a formulation of a room temperature curable organopolysiloxane composition and arrived at a discovery that the composition comprising the above mentioned components (a) to (d), of which the component (b) is the above described novel trifluoropropyl- and alkenyloxy-substituted cyclopolysiloxane, in a limited proportion is very advantageous to be freed from the problems and disadvantages in the RTV silicone rubber compositions of the prior art.

The base component, i.e. the component (a), of the inventive room temperature curable organopolysiloxane composition is a diorganopolysiloxane having a substantially linear molecular structure and terminated at both molecular chain ends each with a hydroxy group directly bonded to the silicon atom. The organic groups in the diorganopolysiloxane are each a substituted or unsubstituted monovalent hydrocarbon group selected from the same class as that for the group denoted by R in the alkenyloxy-containing cyclopolysiloxane. It is preferable that the diorganopolysiloxane as the component (a) has a viscosity of at least 25 centistokes at 25° C. in order that the cured silicone rubber product obtained from the inventive organopolysiloxane composition may have excellent mechanical properties or, in particular, rubbery elasticity.

The component (b) is the trifluoropropyl- and alkenyloxy-substituted cyclopolysiloxane of the general formula (I) in which the suffix n should be 2 or 3 in order that the cyclopolysiloxane may serve as a crosslinking agent of the component (a). The alkenyloxy group $-O-CR^1=CHR^1$ can be an isopropenyloxy, 1-isobutynyloxy, 1-methyl-1-propenyloxy, 1,4-dimethyl-1,3-pentadienyloxy, cyclohexenyloxy or the like group. In the cyclohexenyl group above mentioned, it should be construed that the two $R^1$ groups jointly form a divalent butylene group $-CH_2)_4$ to form a 6-membered ring.

Exemplary of some of the particularly preferable trifluoropropyl- and alkenyloxy-substituted cyclopolysiloxanes are the compounds expressed by the following formulas:

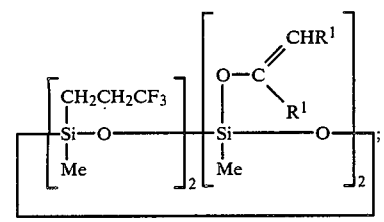

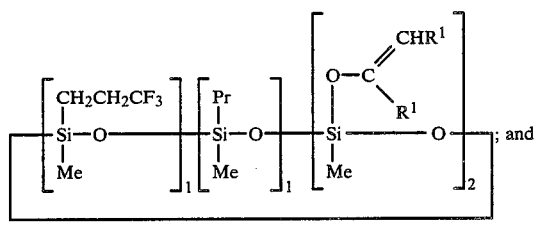

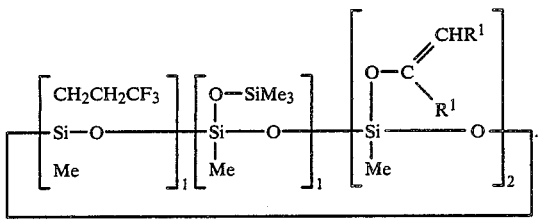

The amount of the component (b) in the inventive organopolysiloxane composition should be in the range from 0.01 to 25 parts by weight or, preferably, from 0.1 to 10 parts by weight per 100 parts by weight of the component (a) in order that the inventive composition can be cured with a sufficiently high velocity and exhibit excellent properties upon curing.

The component (c) is also an alkenyloxy-substituted cyclopolysiloxane of the general formula (II) in which the alkenyloxy group —O—CR¹=CHR¹ may be the same as or different from the alkenyloxy group in the component (b) and selected from the class given as the examples of the alkenyloxy groups in the component (b). The other organic groups denoted by the symbol R and bonded to the silicon atoms may be similar ones to those in the component (b) denoted by the same symbol with exception of 3,3,3-trifluoropropyl group.

Exemplary of some of the particularly preferable cyclopolysiloxane compounds as the component (c) are those expressed by the following structural formulas:

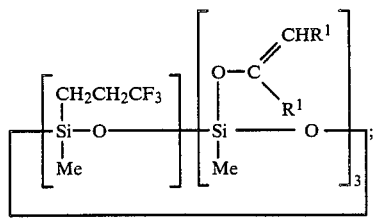

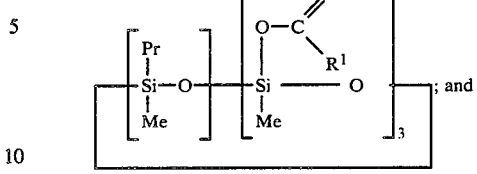

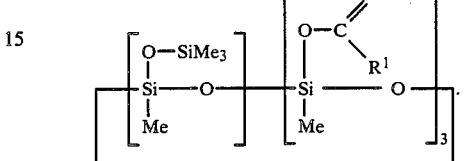

The amount of the component (c) in the inventive organopolysiloxane composition should be in the range from 0.01 to 25 parts by weight or, preferably, from 0.05 to 10 parts by weight per 100 parts by weight of the component (a). When the amount thereof is smaller than 0.01 part by weight, the organopolysiloxane composition has no satisfactory curability while an excessively large amount of this component over 25 parts by weight is detrimental to the rubbery elasticity of the cured composition in addition to the increased shrinkage of the composition by curing.

The polyfunctional cyclic organopolysioloxane as the component (c) can be synthesized by a known method in which a halogenn-containing cyclic organopolysiloxane is reacted with a ketone compound, e.g. acetone, to cause dehydrohalogenation condensation in the presence of a suitable acid acceptor such as triethylamine, dimethylaniline and the like organic amine compounds or metallic sodium and, according to need, by use of a catalyst such as zinc chloride, copper chloride and the like, preferably, in a reaction medium of a polar organic solvent.

The component (d) in the inventive organopolysiloxane composition which serves as a crosslinking promoter is a guanidino-containing silane or polysiloxane compound having, in a molecule, at least one guanidino group represented by the formula (III). The groups denoted by the symbol $R^2$ in the formula are each a hydrogen atom or a monovalent hydrocarbon group. A particularly preferable guanidino group is tetramethylguanidino group of the formula $(Me_2N-)_2C=N-$. The linking organic group between the guanidino group and the silicon atom is not particularly limitative but it is preferably an alkylene or oxyalkylene group.

Exemplary of the particularly preferable guanidino-containing silane or polysiloxanr compounds are those expressed by the following structural formulas:

$(Me_2N-)_2C=N-CH_2CH_2CH_2SiMe_3$;
$(Me_2N-)_2C=N-CH_2CH_2CH_2SiMe_2Ph$;
$(Me_2N-)_2C=N-CH_2CH_2CH_2Si(-O-SiMe_3)_3$;

-continued

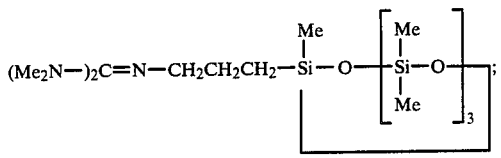

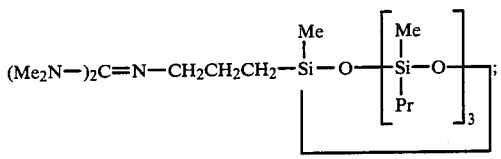

(Me$_2$N—)$_2$C=N—CH$_2$CH$_2$CH$_2$SiMe$_2$—OMe; and
(Me$_2$N—)$_2$C=N—CH$_2$CH$_2$CH$_2$SiMe(—OMe)$_2$.

These guanidino-containing silane or polysiloxane compounds can be readily synthesized by the dehydrohalogenation reaction between guanidine or a substituted guanidine and an organosilane or organopolysiloxane compound having one or more of halogenoalkyl groups in the presence of an acid acceptor.

The amount of this component (d) in the inventive organopolysiloxane composition should be in the range from 0.01 to 5 parts by weight or, preferably, from 0.1 to 2 parts by weight per 100 parts by weight of the diorganopolysiloxane as the component (a). With the amount thereof in excess of the above range, the so-called tack-free time is prolonged when the composition is exposed to the atmospheric moisture to form a surface film without tackiness and the curability of the composition in the depth of a thick layer cannot be improved. When the amount of the component (d) is too large, on the other hand, the organopolysiloxane composition is sometimes subject to the problem of coloration of the cured composition under heating due to the presence of the guanidino group of the formula (III).

The room temperature curable organopolysiloxane composition of the invention is prepared by uniformly blending the above described components (a) to (d) with optional admixture of a filler which may be inorganic or organic. Suitable fillers are exemplified by the inorganic ones such as finely pulverized quartz and fused quartz glass, silica aerogel, precipitated silica, diatomaceous earth, oxides of metals, e.g. iron oxides, zinc oxide and titanium dioxide, carbonates of metals, e.g. calcium carbonate, magnesium carbonate and zinc carbonate, asbestos, glass wool, carbon black and finely powdered mica as well as those obtained by the surface treatment of these inorganic fillers with a suitable organosilane or fatty acid compound and organic ones such as finely pulverized synthetic resins, e.g. polystyrene, polyvinyl chloride and polypropylene. The amount of the filler to be added to the inventive organopolysiloxane composition should not exceed 400 parts by weight or, preferably, 200 parts by weight per 100 parts by weight of the diorganopolysiloxane as the component (a). The filler should be dried as completely as possible before incorporation into the inventive composition in order to avoid any adverse effect of the moisture content on the curing performance of the composition.

Furthermore, it is of course optional that the inventive organopolysiloxane composition may be admixed with various kinds of additives conventionally used in similar RTV silicone rubber compositions including, for example, pigments, dyes, thixotropy-improvers, aging retarders, antioxidants, antistatic agents, flame retardant agents, e.g. antimony oxide and chlorinated paraffins, heat condutivity improvers, e.g. boron nitride, lubricants, e.g. fatty acid salts, metal alcoholates, so-called carbon-functional silanes having amino, epoxy, thionyl and other functional groups and the like according to need.

The above described inventive organopolysiloxane composition with optional admixture of various additives described above is stable when kept under a hermetically sealed condition and storable over a long period of time without denaturation. When exposed to atmospheric air containing moisture, the composition is rapidly cured into a rubbery elastomer by the interaction with the atmospheric moisture. In this case, firm adhesion of the cured composition is obtained with the surface of the substrate of various kinds of materials or, in particular, metals on which the composition is cured. Advantageously, no toxic or corrosive gases are formed by the curing of the inventive composition so that any metallic substrates are freed from the problem of rusting and the working environment may not be under so powerful ventilation as in the use of conventional RTV silicone rubber compositions. Further characteristically, the curing of the inventive composition is rapid not only in the surface layer but also in the depth of a thick layer and the cured rubbery elastomer thereof has a large ultimate elongation in the tensile test.

Accordingly, the inventive room temperature curable organopolysiloxane composition is useful as such as a sealing or caulking material, coating material, adhesive and the like. The composition may be diluted with a suitable organic solvent such as hydrocarbons, e.g. toluene, xylene, petroleum ether and the like, ketones and esters when it is desired to use the composition as a water-repellent agent, fiber-treatment agent, mold-release agent and the like.

Following are the examples to illustrate the novel cyclic organopolysiloxane of the invention substituted simultaneously with trifluoroalkyl and alkenyloxy groups as well as the room temperature curable organopolysiloxane composition formulated therewith in more detail.

EXAMPLE 1

Into a four-necked flask of 2-liter capacity equipped with a reflux condenser, stirrer rod, thermometer and gas inlet tube for introduction of chlorine were taken 800.0 g of 1,3,5,7-tetramethyl cyclotetrasiloxane and 800.0 g of carbon tetrachloride and chlorine gas was introduced into the reaction mixture for 6 hours under agitation and cooling with water from outside of the flask. After the above mentioned reaction time, carbon tetrachloride was removed from the reaction mixture by distillation under reduced pressure to give 366.9 g of a mixture (referred to as H$_4$Cl$_2$) of 1,3,5,7-tetramethyl-1,3-dichlorocyclotetrasiloxane and 1,3,5,7-tetramethyl-1,5,-dichlorocyclotetrasiloxane boiling at 87° to 88° C. under a pressure of 30 mmHg corresponding to 35.6% of the theoretical yield and 156.3 g of 1,3,5,7-tetramethyl-1,3,5-trichlorocyclotetrasiloxane (referred to as H$_4$Cl$_3$) boiling at 74° to 75° C. under a pressure of 8 mmHg corresponding to 13.7% of the theoretical yield.

In the second place, 309.4 g of the above obtained dichlorocyclotetrasiloxane mixture and 0.3 g of a 2% octanol solution of chloroplatinic acid-octanol complex were taken into a four-necked flask of 500 ml capacity equipped with a dry ice cooler, stirrer rod, thermometer and gas inlet tube and 3,3,3-trifluoropropene gas was introduced into the reaction mixture kept at 120° C. under agitation for 6 hours. After completion of the reaction, the reaction mixture was subjected to fractional distillation to give 186.8 g of a fraction boiling at 109° to 110° C. under a pressure of 2 mmHg.

This product was identified by the gas-chromatographic mass spectrometry and elementary analysis to be a trifluoropropyl-substituted cyclotetrasiloxane of the following formula:

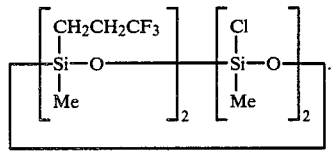

The yield of this compound, which is referred to as $HF_4{}_2Cl_2$ hereinbelow, was 37.2% of the theoretical value and the results of the analyses were as follows.

The m/e value of the principal peak in the GC-MS spectrum: 501 (molecular weight calculated for $C_{10}H_{20}O_4Si_4Cl_2F_6$: 501.5)

| Elementary analysis: | C | H | Si |
|---|---|---|---|
| Calculated, % | 23.9 | 4.0 | 22.4 |
| Found, % | 23.7 | 3.9 | 22.7 |

The following step, i.e. the third step, was the isopropenyloxylation reaction of the above obtained $HF_4{}_2Cl_2$. Thus, 420.0 g of acetone, 84.0 g of N,N-dimethylformamide, 0.6 g of copper (I) chloride and 78.0 g of triethylamine were introduced into a four-necked flask of 1 liter capacity equipped with a reflux condenser, stirrer rod, thermometer and dropping funnel to form a reaction mixture. Into the reaction mixture heated at 60° C., 150.4 g of the $HF_4{}_2Cl_2$ were added dropwise under agitation over a period of 30 minutes followed by heating at the same temperature for 8 hours under continuous agitation to complete the reaction. After completion of the reaction, the salt precipitated in the reaction mixture was separated by filtration and the filtrate was distilled under reduced pressure to give 65.0 g of a fraction boiling at 115° to 118° C. under a pressure of 2 mmHg and having a refractive index of 1.408 at 25° C.

The above obtained product was analyzed by the infrared absorption spectroscopy, gas-chromatographic mass spectrometry and elementary analysis and identified to be the compound expressed by the following structural formula:

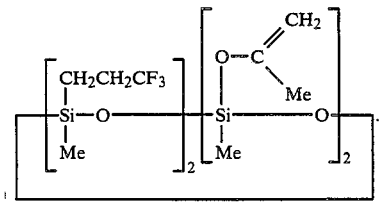

The above given yield of the compound was 40.2% of the theoretical value and the infrared absorption spectrum of the compound is given in FIG. 1. The results of the GC-MS analysis and the elementary analysis were as follows.

The m/e value of the principal peak in the GC-MS spectrum: 544 (molecular weight calculated for $C_{16}H_{30}O_6Si_4F_6$: 544.7)

| Elementary analysis: | C | H | Si |
|---|---|---|---|
| Calculated, % | 35.3 | 5.6 | 20.6 |
| Found, % | 35.2 | 5.4 | 20.7 |

EXAMPLE 2

The addition reaction of 3,3,3-trifluoropropene and the $H_4Cl_3$, i.e. 1,3,5,7-tetramethyl-1,3,5-trichlorocyclotetrasiloxane, obtained in the first step of Example 1 was undertaken in a similar manner to the second step of the same example and 314.2 g of the thus obtained addition product were subjected to the isopropenyloxylation reaction in a similar manner to the third step of Example 1 to give 208.3 g of a fraction boiling at 125° to 127° C. under a pressure of 2 mmHg and having a refractive index of 1.395 at 25° C.

This compound was identified by the infrared absorption spectrometry, gas-chromatographic mass spectrometry and elementary analysis to be the compound expressed by the following structural formula:

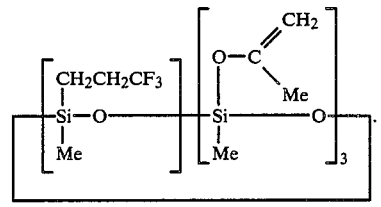

The above mentioned yield of the compound was 57.8% of the theoretical value.

Figure 2:
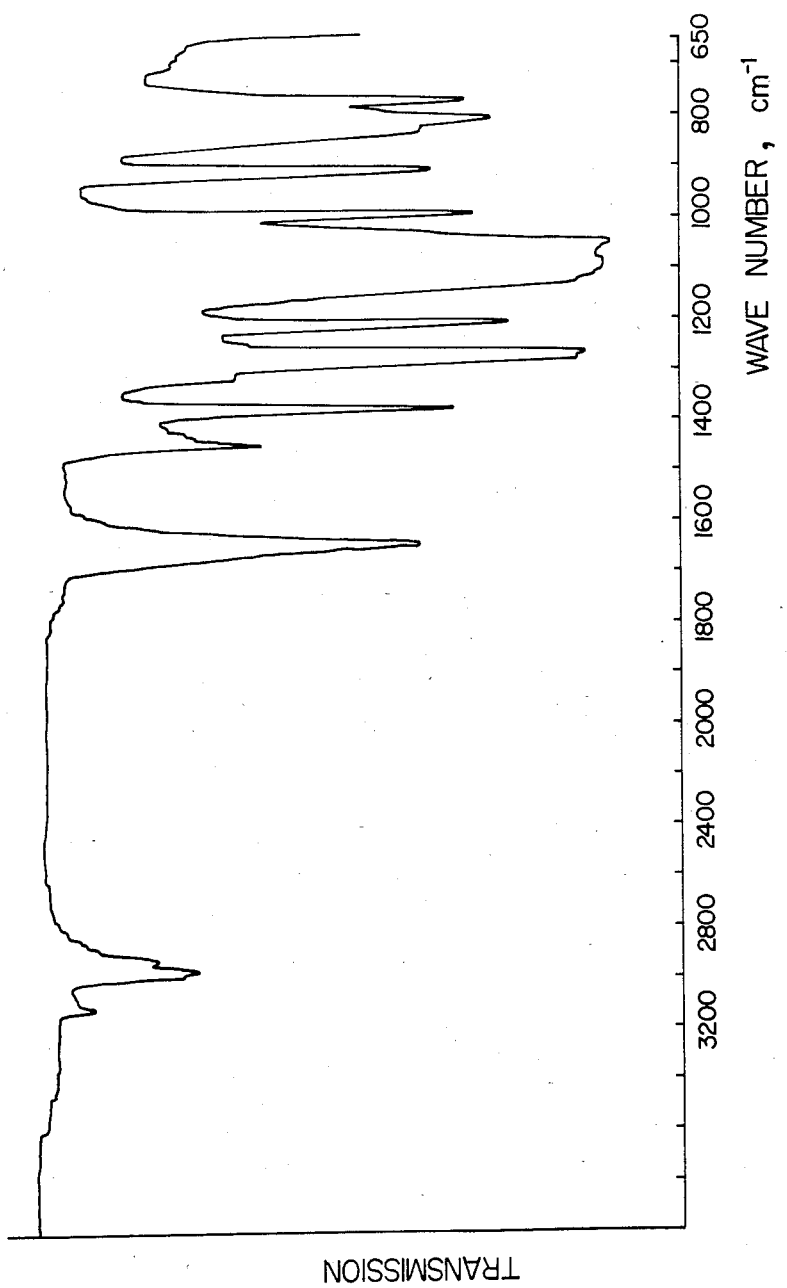

The infrared absorption spectrum of the compound is shown in FIG. 2. The results of the GC-MS analysis and the elementary analysis were as follows.

The m/e value of the principal peak in the GC-MS spectrum: 504 (molecular weight calculated for $C_{16}H_{31}O_7Si_4F_3$: 504.8)

| Elementary analysis: | C | H | Si |
|---|---|---|---|
| Calculated, % | 38.1 | 6.2 | 22.3 |
| Found, % | 38.0 | 6.3 | 22.2 |

EXAMPLE 3

The $H_4Cl_2$ obtained in the first step of Example 1 was subjected to a partial addition reaction of 3,3,3-trifluoropropene in a similar manner to the second step of the same example followed by the addition reaction of propylene and 305.6 g of the addition product thus obtained were subjected to the isopropenyloxylation reaction in a similar manner to the third step of Example 1 followed by distillation under reduced pressure to give 216.4 g of a fraction boiling at 130° to 132° C. under a pressure of 2 mmHg and having a refractive index of 1.405 at 25° C.

This compound was identified by the infrared absorption spectrometry, gas-chromatographic mass spectrometry and elementary analysis to be the compound expressed by the following structural formula:

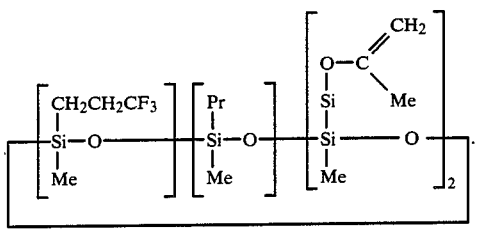

The above mentioned yield of the compound was 64.6% of the theoretical value.

Figure 3:
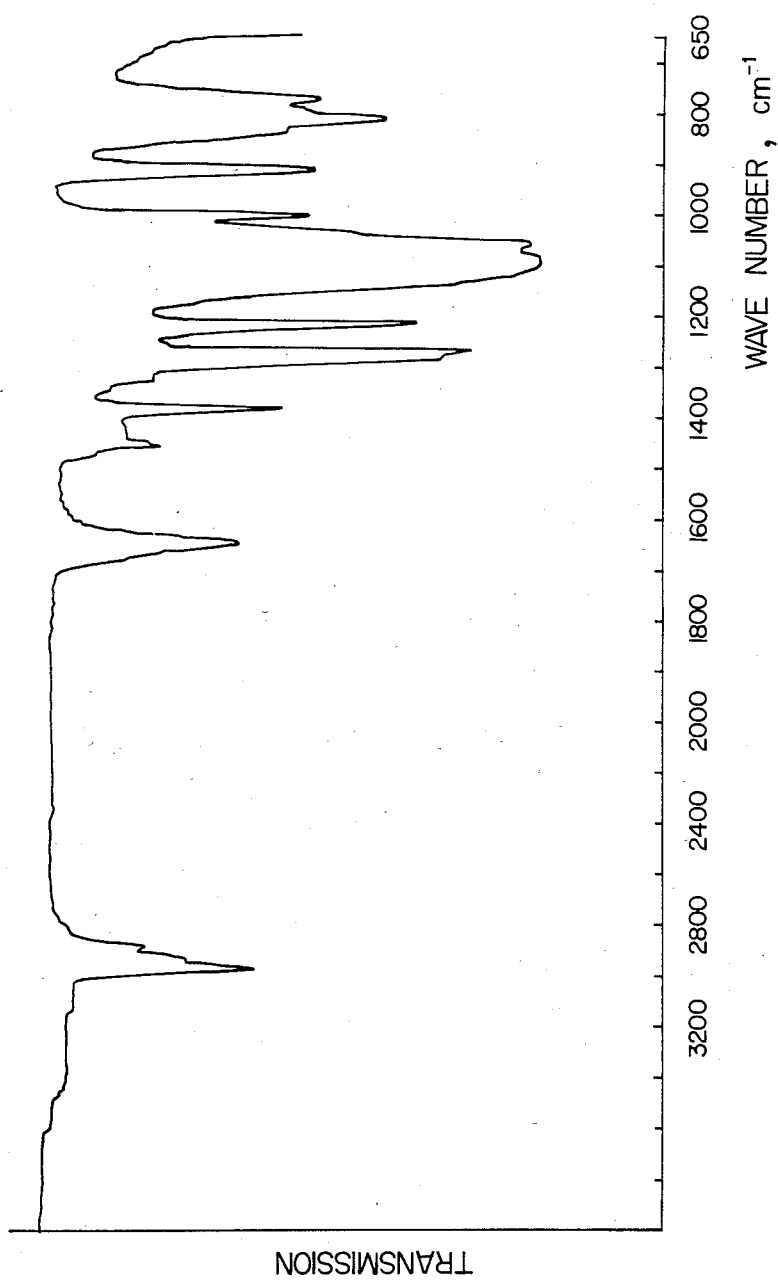

The infrared absorptiion spectrum of the compound is shown in FIG. 3. The results of the GC-MS analysis and the elementary analysis were as follows.

The m/e value of the principal peak in the GC-MS spectrum: 490 (molecular weight calculated for $C_{16}H_{33}O_6Si_4F_3$: 490.8)

| Elementary analysis: | C | H | Si |
|---|---|---|---|
| Calculated, % | 39.2 | 6.8 | 22.9 |
| Found, % | 39.3 | 6.6 | 23.1 |

EXAMPLE 4

Into a four-necked flask of 2 liter capacity equipped with a reflux condenser, stirrer rod, thermometer and gas inlet tube for chlorine were taken 1000 g of 1,3,5,7-tetramethyl trimethylsiloxy cyclotetrasiloxane and 1000 g of carbon tetrachloride and chlorine gas was introduced into this reaction mixture under cooling with water and agitation for 6 hours to effect the chlorination reaction. After completion of the reaction, the carbon tetrachloride was removed by distillation from the reaction mixture, which was then subjected to distillation under reduced pressure to give 263.0 g of a fraction boiling at 119° to 121° C. under a pressure of 30 mmHg. This fraction was identified to be the compound expressed by the following formula and the above mentioned yield of the compound was 21.7% of the theoretical value:

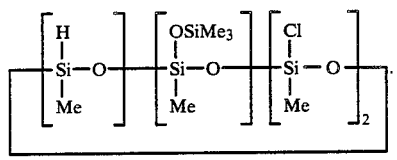

The thus obtained chlorination product was subjected to the addition reaction of 3,3,3-trifluoropropene in a similar manner to the second step of Example 1 and then 250.0 g of the thus obtained addition product were further subjected to the isopropenyloxylation reaction in a similar manner to the third step of the same example followed by distillation of the reaction product under reduced pressure to give 113.3 g of a fraction boiling at 121° to 123° C. under a pressure of 1 mmHg and having a refractive index of 1.401 at 25° C.

This compound was identified by the infrared absorption spectrometry, gas-chromatographic mass spectrometry and elementary analysis to be the compound expressed by the following structural formula and the above mentioned yield of the compound was 41.6% of the theoretical value:

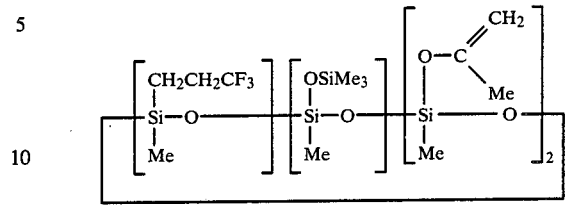

The infrared absorption spectrum of this compound is shown in FIG. 4. The results of the GC-MS analysis and the elementary analysis of the compound were as follows.

The m/e value of the principal peak in the GC-MS spectrum: 536 (molecular weight calculated for $C_{17}H_{35}O_7Si_5F_3$: 536.9)

| Elementary analysis: | C | H | Si |
|---|---|---|---|
| Calculated, % | 35.8 | 6.6 | 26.2 |
| Found, % | 35.7 | 6.7 | 26.4 |

EXAMPLE 5

A base compound was prepared by blending 60 parts by weight of a dimethylpolysiloxane terminated at both molecular chain ends each with a hydroxy group directly bonded to the silicon atom and having a viscosity of 5700 centistokes at 25° C. and 40 parts by weight of a calcium carbonate filler surface-treated with a fatty acid and kneading the blend by passing once through a triple-roller mill.

The base compound was further admixed with 1.8 parts by weight of a trifluoropropyl- and alkenyloxy-substituted cyclic organopolysiloxane of the formula

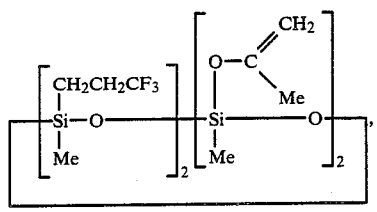

0.2 part by weight of an alkenyloxy-substituted cyclic organopolysiloxane of the formula

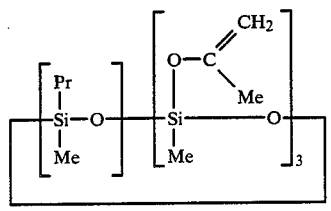

and 0.5 part by weight of 3-(tetramethylguanidino)propyl trimethyl silane of the formula $(Me_2N-)_2C=N-CH_2CH_2CH_2SiMe_3$ to give a uniform room temperature curable composition.

The thus prepared curable composition was spread in a sheet of 2 mm thickness which was kept standing for 7 days at 20° C. in an atmosphere of 55% relative humidity. It was noted that curing of this sheeted curable composition proceeded simultaneously in the surface layer and in the core portion of the sheet by the interaction with the atmospheric moisture. This rubbery elastomer sheet of the cured composition was subjected to the measurement of the mechanical properties as cured and after thermal aging by heating at 120° C. for 7 days to give the results tabulated below.

|  | As cured | After thermal aging |
|---|---|---|
| Hardness (JIS K 6301) | 14 | 14 |
| Tensile strength, kg/cm$^2$ (JIS K 6301) | 10 | 11 |
| Ultimate elongation, % (JIS K 6301) | 1060 | 981 |
| Adhesion strength, kg/cm$^2$ (JIS A 5758) | at least 4.1 | at least 4.1 |

EXAMPLE 6

The experimental procedure was substantially the same as in the preceding Example 5 except that the trifluoropropyl- and alkenyloxy-substituted cyclic organopolysiloxane used in this example was the compound prepared in Example 4 and the isopropenyloxy- and propyl-substituted cyclic organopolysiloxane used in Example 5 was replaced with the same amount of a trimethylsiloxy- and isopropenyloxy-substituted cyclic organopolysoiloxane expresed by the following structural formula:

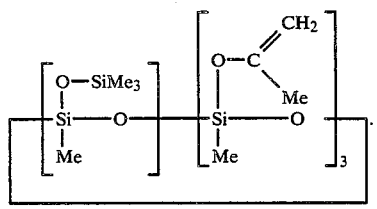

The results of the determination of the mechanical properties of the cured rubber sheet were as tabulated below either as cured or after thermal aging at 120° C. for 7 days.

|  | As cured | After thermal aging |
|---|---|---|
| Hardness | 14 | 14 |
| Tensile strength, kg/cm$^2$ | 9 | 10 |
| Ultimate elongation, % | 940 | 900 |
| Adhesion strength, kg/cm$^2$ | at least 4.1 | at least 4.1 |

EXAMPLE 7

A base compound was prepared by uniformly blending under an anhydrous condition in an air-tight blender machine 60 parts by weight of the same hydroxy-terminated diorganopolysiloxane as used in Example 5 and 40 parts by weight of a calcium carbonate filler dried for 2 hours at 110° C. in an atmosphere of nitrogen gas followed by a surface treatment with a fatty acid. The base compound was then admixed with 7.2 parts by weight of the same trifluoropropyl- and isopropenyloxy-substituted cyclic organopolysiloxane used in Example 5, 0.8 part by weight of the same trimethylsiloxy- and isopropen-yloxy-substituted cyclic organopolysiloxane as used in Example 6 and 1.0 part by weight of a guanidino-containing silane compound 3-(tetramethylguanidino)propyl tris(trimethylsiloxy)silane also under an anhydrous condition followed by deaeration of the entrained air. The thus prepared organopolysiloxane composition was quite stable under a hermetically sealed condition over a period of 6 months or longer without coloring or discoloration.

After storage for 6 months under a sealed condition, the composition was spread in a 2 mm thick sheet to be cured into a rubbery elastomer in the same manner as in Example 5, of which the mechanical properties were determined as cured or after thermal aging at 120° C. for 7 days to give the results tabulated below.

|  | As cured | After thermal aging |
|---|---|---|
| Hardness | 16 | 17 |
| Tensile strength, kg/cm$^2$ | 11 | 13 |
| Ultimate elongation, % | 960 | 910 |
| Adhesion strength, kg/cm$^2$ | at least 4.3 | at least 4.2 |

Further, a galss dish of 12 mm depth was filled with the above prepared organopolysiloxane composition and kept standing at 20° C. in an atmosphere of 55% relative humidity to examine the curing velocity from the surface to the depth and the adhesion strength according to the procedure specified in JIS A 5758. The results were that the curing of the composition proceeded at a velocity of 2 to 3 mm per day and the adhesion of the cured composition was very firm to the surfaces of glass, aluminum, copper and epoxy resin as the substrate on which the composition had been cured.

EXAMPLE 8

The curable organopolysiloxane composition prepared in Example 5 was put into a joint space of 2 cm by 25 cm by 1 cm dimensions formed between two marble stone blocks of each 25 cm by 25 cm by 2 cm placed 1 cm apart side by side to fill up the space and kept standing for days in an ambient atmosphere to be cured.

The surface of the cured rubbery composition was free from "pitting" which is sometimes unavoidable in a similar room temperature curable organopolysiloxane composition caused by the floating and appearance of air bubbles entrained therein by blending in the course of preparation on the surface along with the shrinkage of the composition by curing. Furthermore, this test specimen of two marble stone blocks jointed together by the cured organopolysiloxane composition was subjected to outdoor exposure for 120 days including 24 times of rainfalls to give an accumulated rain precipitation of 181 mm, during which period the accumulated energy of sun light falling on and received by a horizontally placed surface amounted to 15,535 Cal/cm$^2$ composed of 1290 Cal/cm$^2$ by the ultraviolet of the wavelength 300 to 400 nm, 7246 Cal/cm$^2$ by the visible of the wavelength 400 to 700 nm and 6999 Cal/cm$^2$ by the infrared of the wavelength 700 to 1200 nm. The result was that absolutely no stain assumably caused by the organopolysiloxane composition in the joint was found on the surface of the test specimen near the jointed portion.

Further, a cylindrical polyethylene vessel having a depth of 70 mm was filled with the organopolysiloxane composition and kept standing for 24 hours at 20° C. in an atmosphere of 55% relative humidity to find that the composition was cured into a rubbery elastomer seemingly at the same curing velocity in the surface and core portions. Accordingly, the hardness of the thus cured rubber was determined as a measure of the extent of curing by use of an Ascar Hardness Tester, "Dyna C" to give the results that the hardness was 41 for the surface portion and 40 and for the bottom portion of 70 mm depth.

EXAMPLE 9

A room temperature curable organopolysiloxane composition was prepared by blending 100 parts by weight of the base compound prepared in Example 6, 1.8 parts by weight of the trifluoropropyl- and isopropenyloxy-substituted cyclic organopolysiloxane prepared in Example 2 and 0.5 part by weight of 3-(tetramethylguanidino)propyl tris(trimethylsiloxy)silane.

The thus prepared curable composition was cured into a rubber sheet, of which the mechanical properties were determined in the same manner as in Example 5 either as cured or after thermal aging at 120° C. for 7 days to give the results tabulated below.

|  | As cured | After thermal aging |
|---|---|---|
| Hardness | 16 | 17 |
| Tensile strength, kg/cm$^2$ | 11 | 11 |
| Ultimate elongation, % | 810 | 790 |
| Adhesion strength, kg/cm$^2$ | at least 4.2 | at least 4.1 |

What is claimed is:

1. A cyclic organopolysiloxane compound represented by the general formula

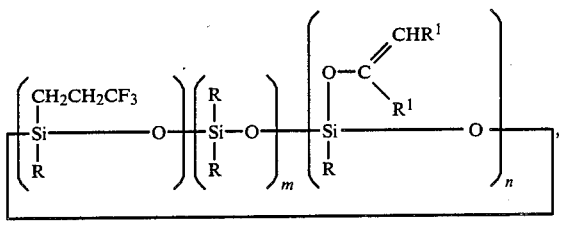

in which the groups denoted by R are each a halogen- or cyano-substituted or unsubstituted monovalent hydrocarbon group having from 1 to 8 carbon atoms or a trimethylsiloxy group independently from the others, the groups denoted by R$^1$ are each a hydrogen atom or a substituted or unsubstituted monovalent hydrocarbon group having from 1 to 8 carbon atoms independently from the other, the suffix m is a number of 0, 1 or 2 and the suffix n is a number of 1, 2 or 3 with the proviso that m+n is 3 or 4.

2. The cyclic organopolysiloxane as claimed in claim 1 wherein the suffix n has a value of 2 or 3.

* * * * *